United States Patent
Yoshpa

(10) Patent No.: US 6,537,591 B2
(45) Date of Patent: Mar. 25, 2003

(54) AQUATIC ANIMAL TREATMENT METHOD AND COMPOSITION CONTAINING PIMENTA EXTRACT

(75) Inventor: Michael Yoshpa, Doylestown, PA (US)

(73) Assignee: Aquarium Pharmaceuticals, Inc., Chalfont, PA (US)

( * ) Notice: Subject to any disclaimer, the term of this patent is extended or adjusted under 35 U.S.C. 154(b) by 0 days.

(21) Appl. No.: 09/797,744

(22) Filed: Mar. 2, 2001

(65) Prior Publication Data

US 2002/0164384 A1 Nov. 7, 2002

(51) Int. Cl.⁷ ............................................. A61K 35/78
(52) U.S. Cl. ....................... 424/725; 424/734; 424/776
(58) Field of Search ................................. 424/725, 734

(56) References Cited

U.S. PATENT DOCUMENTS

| | | |
|---|---|---|
| 134,808 A | 1/1873 | Kintz |
| 4,060,602 A | 11/1977 | Haas et al. |
| 5,135,746 A | 8/1992 | Matsuno et al. |
| 5,629,021 A | 5/1997 | Wright |
| 5,804,199 A | 9/1998 | Aasjord et al. |
| 5,882,647 A | 3/1999 | Yoshpa |
| 5,906,825 A * | 5/1999 | Seabrook, Jr. et al. |

FOREIGN PATENT DOCUMENTS

| | | | |
|---|---|---|---|
| JP | 401075422 A | | 3/1989 |
| JP | 401075424 A | | 3/1989 |
| JP | 401075425 A | | 3/1989 |
| JP | 06032741 A | * | 2/1994 |
| JP | 6(1994)-32741 | | 2/1994 |

OTHER PUBLICATIONS

The Herb Society of America—Encyclopedia of Herbs & Their Uses, Dorling Kindersley, Ed., cover page and p. 162 (1995).

Duke, James A., 233. *Myrica Cenifera* L. and Other SP (Myricaeae)—Bayberry, Wax Myrtle, *CRC Handbook of Medicinal Herbs,* CRC Press, Inc. Boca Raton, Florida, Cover Page and pp. 317–318 (1995).

"*Myrica rubra*—Cultivation Notes," GardenBed.com: *Myrica rubra*, 2 pages; from http://www.gardenbed.com/m/2419.cfm, printed Oct. 3, 2001.

Grieve, M., "A Modern Herbal—Bayberry," Botanical.com, 3 pages; from http://www.botanical.com/botanical/mgmb/b/bayer20.html. printed Oct. 3, 2001.

St. Angelo, "Food Emulsifiers—Chemistry, Technology, Functional Properties and Applications," G. Charalambous & G. Doxastakis, Ed., *Development in Food Science,* 19:1–8 (1989).

Albert Y. Leung & Steven Foster, *Encyclopedia of Common Natural Ingredients Used in Food, Drugs, and Cosmetics,* 2nd Ed., pp. 20–22 (Allspice) and 71–72 (Bay, West Indian), John Wiley & Sons, Inc., (1996).

Julia Lawless, *The Illustrated Encyclopedia of Essential Oils,* Barnes & Noble Books, NY, pp. 194, 195 (1995).

Deni Brown, *The Herb Society of America Encyclopedia of Herbs & Their Uses,* Dorling Kindersley, Ed., p. 328 (1995).

James A. Duke, Ph.D., *CRC Handbook of Medicinal Herbs,,* CRC Press, Inc. Boca Raton, FL, p. 371 (1995).

Arthur O. Tucker et al., "Volatile Leaf Oils of Caribbean Myrtaceas. I. Three Varieties of *Pimenta racemosa* (Miller) J. Moore of the Dominican Republic and the Commercial Bay Oil," *J. Ess. Oil Res.,* 3:323–329 (Sep./Oct. 1991).

Arthur O. Tucker et al., "Volatile Leaf Oils of Caribbean Myrtaceae. II. *Pimenta dioica* (L.) Merr. of Jamaica," *J. Ess. Oil Res.,* 3:195–196 (May/Jun. 1991).

Guylene S. Aurore et al., "Antibacterial and Antifungal Activites of the Essential Oils of *Pimenta racemosa* var. racemosa P. Miller (J.W.MOore) (Myrtaceae)," *J. Essent. Oil Res.,* 10:161–164 (Mar./Apr. 1998), XP008008597;.

K.A. Hammer et al., "Antimicrobial activity of essential oils and other plant extracts," *Journal of Applied Microbiology,* 86:985–990 (1999), XP–001108841;.

Quitterie Delespaul et al., "The Antifungal Activity of Essential Oils as Determined by Different Screening Methods," *J. Essent. Oil Res.,* 12:256–266 (Mar./Apr. 2000), XP008008596;.

D. McHale et al., "Composition of West Indian Bay Oils," *Food Chemistry, Elsevier Science Publishers Ltd, GB,* 2(1):19–25 (1977), XP008008592;.

Ono Yoshihiro, "Exterminator For Parasitic Insect Pest of Pet Animal and Exterminating Apparatus Therefor," *Patent Abstracts of Japan,* Publication No. 10120519 A (Osaka Seiyaku:KK), published May 12, 1998. Abstract Only.

* cited by examiner

Primary Examiner—Leon B. Lankford, Jr.
Assistant Examiner—Ruth Davis
(74) Attorney, Agent, or Firm—Akin, Gump, Strauss, Hauer & Feld, L.L.P.

(57) ABSTRACT

A therapeutic method for treating diseased or injured fish or other aquatic animal includes administering to the fish or other aquatic animal an amount of Pimenta extract selected from the group consisting of *Pimenta racemosa* and *Pimenta dioica* sufficient to promote recovery of the diseased or injured fish or other aquatic animal. Also disclosed is a prophylactic method for treating a disease-free fish or other aquatic animal, including adding to water containing or to contain the fish or other aquatic animal Pimenta extract selected from the group consisting of *Pimenta racemosa* and *Pimenta dioica* in an amount effective to promote resistance of the aquatic animal to disease. An aqueous emulsion containing Pimenta extract oil in water, where the Pimenta extract is selected from the group consisting of *Pimenta racemosa* and *Pimenta dioica* is also disclosed for use in these methods.

27 Claims, No Drawings

AQUATIC ANIMAL TREATMENT METHOD AND COMPOSITION CONTAINING PIMENTA EXTRACT

BACKGROUND OF THE INVENTION

The present invention is directed to the therapeutic and prophylactic treatment of aquatic animals, and more particularly, to the treatment of fish and other aquatic animals with a composition containing, as the active ingredient, an extract of *Pimenta racemosa* (West Indian bay oil) or *Pimenta dioica* (allspice).

Fish diseases and injuries are not only detrimental to the physiological well being of fish, but also can adversely affect the physical appearance of otherwise viable fish. The prevention, control and treatment of fish diseases and fish injuries is particularly important for fish that are kept in artificial or confined environments, such as aquariums, ornamental ponds or aquaculture ponds, as well as various types of shipping containers or holding tanks used for ornamental or food fish, or other aquatic animals.

Fish that are netted, handled or otherwise placed in stressful situations, e.g., under crowded, low oxygen, high carbon dioxide, contaminated water or fluctuating temperature conditions, become more vulnerable to disease, such as those of bacterial or fungal origin. When fish are transported in high concentrations and/or in small volumes of water, they are often subject to trauma or injury, such as being scraped, lacerated, bitten, burned or otherwise wounded. Such shipping conditions may also expose fish to contaminated water, e.g., from natural waste products of fish and from decaying food and dead fish. Contaminated water is also an environment favoring the growth of pathogens that cause fish diseases.

Fish disease therapies that avoid the use of potent drugs or chemicals with adverse side effects, or that avoid the necessity for precise dosing requirements, are desirable for fish in confined environments. While isolation and treatment only of the specific diseased or injured fish is preferred, as a practical matter, such isolated treatment is not often possible, resulting also in exposure of healthy fish to the treatment. Consequently, treatment of individual diseased or injured fish usually entails exposure of healthy fish and all other beneficial organisms in the environment to the treatment composition as well. For this reason, therapeutic treatments for diseased or injured fish that utilize naturally derived substances, which are not injurious to other aquatic animals or plants also present in the water, are particularly preferred.

The treatment of damaged fish tissue in fish with Aloe vera is described by Goldstein in U.S. Pat. No. 4,500,510, assigned to the assignee of the present invention. Yoshpa, in U.S. Pat. No. 5,882,647, also assigned to the assignee of the present invention, discloses treating injured or diseased fish and other aquatic animals using cajeput oil.

The prevention and treatment of bacterial diseases in fish with eucalyptus extract is described in Japanese Patent Publication 04-360839. Eucalyptus extract is a complex mixture obtainable from leaves of Eucalyptus species trees, and the primary component of eucalyptus oil is 1,8-cineole (about 70–85%), sometimes also called eucalyptol.

The present invention is based on the unexpected discovery that extracts of *Pimenta racemosa*, commonly called West Indian bay oil, or *Pimenta dioica*, commonly called allspice, are highly efficacious in the therapeutic treatment of fish and other aquatic animals.

BRIEF SUMMARY OF THE INVENTION

One aspect of the present invention relates to a therapeutic method for treating an aquatic animal comprising administering a composition comprising a Pimenta extract selected from the group consisting of *Pimenta racemosa* and *Pimenta dioica* to a diseased or injured aquatic animal, in an amount effective to promote recovery of such a diseased aquatic animal.

Another aspect of the invention relates to a prophylactic method for treating a disease-free aquatic animal, comprising adding to water containing the aquatic animal, Pimenta extract selected from the group consisting of *Pimenta racemosa* and *Pimenta dioica* in an amount effective to promote resistance of the aquatic animal to disease.

Yet another aspect of the invention is a composition for the treatment of an aquatic animal, the composition comprising Pimenta extract selected from the group consisting of *Pimenta racemosa* and *Pimenta dioica*, and preferably, an aqueous mixture or an aqueous emulsion including the Pimenta extract.

The method and composition are useful for treating fish of all types and species and other aquatic animals afflicted with, subjected to or susceptible to bacterial disease, fungal disease, or injuries, such as wounds, lacerations, abrasions, burns and the like. The Pimenta extract is preferably administered by introducing the Pimenta extract into the water that contains or will contain the aquatic animal to be treated.

DETAILED DESCRIPTION OF THE INVENTION

The term "disease" and other similar terms as used herein are intended to cover diseases of bacterial or fungal origin, to which fish or other aquatic animals are susceptible. The term "injury" and other similar terms as used herein are intended to cover trauma or injuries, such as wounds, e.g., lacerations, tears and bites, as well as scrapes, abrasions, burns or the like to which fish or other aquatic animals are susceptible. Rapid healing of such injuries is often slowed, delayed or precluded by the presence of pathogenic organisms in the water environment harboring the fish or other aquatic animal or in the diseased or injured skin, tissue, organ or other part of the fish or other aquatic animal.

The active ingredient for the aquatic animal treatment method and composition of this invention is an extract from the plants of the genus Pimenta and, more particularly, bay or allspice. As used herein, the term "Pimenta extract" means extracts of the genus Pimenta selected from the group consisting of the species *Pimenta racemosa* and *Pimenta dioica*. "Pimenta extract" will be used to refer broadly to the active ingredient of the composition and method of the present invention.

As used herein, "bay," sometimes called West Indian bay oil, or Myrcia, or bay rum tree oil, is the substance that is obtainable from the tree *Pimenta racemosa* (Mill.) J. W. Moore (syn. *P. acris* Kostel) (Family Myrtaceae), which is indigenous to the West Indies, and is cultivated in Venezuela, Puerto Rico and the Caribbean Islands. Bay contains a large number of components, most of which are terpenoids, and major components being eugenol (up to about 56%), chavicol (up to about 22%) and myrcene (up to about 21%). Other components in lesser amounts include 1,8-cineole, limonene, isoeugenol, linalool, methyl eugenol (3,4-dimethoxyallylbenzene), estragole (methyl chavicol), α-terpineol and others.

There are several varieties of bay, including anise-scented, lemon-scented and clove-scented varieties. The distinctions among the varieties include different proportions of the components noted above, for example, the anise-scented variety contains methyl eugenol (about 43%) and methyl chavicol (about 32%) as the major components, and the lemon-scented variety contains mostly citral (greater than about 80%).

Although the commonly used domestic spice is sometimes also referred to as "bay" in the literature, this spice is sweet bay (*Laurus nobilis*), and not West Indian bay used in the present invention. This is an important distinction.

As used herein, "allspice", sometimes called pimenta, Jamaica pepper and pimento, is the substance that is obtainable from the tree *Pimenta dioica* (L.) Merr. (syn. *P. officinalis* Lindl.; Eugenia Pimenta DC.) (Family Myrtaceae). This tree is native to the West Indies, Central America and Mexico. The parts of the plant that are primarily used for the extract are the dried, full-grown but unripe fruit, and the leaves. Major producers are found in Jamaica and Cuba. Allspice contains about 4% volatile oil, but storage of undried berries under conditions that prevent rapid removal of moisture can increase the volatile oil content by up to 50%. The major component of the volatile oil (known as pimenta, pimento or allspice oil) is eugenol (about 60%–about 80%). Other constituents include methyl eugenol, 1,8-cineol, l-α-phellandrene, caryophyllene and 2 epimeric 10-cadinols (about 2%). There are more than 36 constituents comprising the volatile oil component of allspice. Beside volatile oil, other constituents of allspice include quercetin, glycosides, catechins, proanthocyanidins, proteins, lipids, carbohydrates, vitamins (A, C, thiamine, riboflavin, niacin) and minerals. The leaf oil (pimento leaf oil) contains more eugenol (up to about 96%) than the berry oil, and is similar in composition to clove leaf oil.

It is important to note that the active ingredient utilized in this invention is a complex mixture of components normally and naturally found in extracts of the species *Pimenta racemosa* or *Pimenta dioica* of the Pimenta genus, West Indian bay oil and allspice, rather than a single component fractionally distilled and separated from such sources, e.g., eugenol. West Indian bay oil is produced in commercial quantities in Venezuela, Puerto Rico, and the Caribbean Islands. Allspice is produced in commercial quantities in Jamaica, Cuba and elsewhere in the West Indies, Central America and Mexico. The Pimenta extract used in the present invention is readily available from commercial suppliers of naturally derived food and cosmetic oils and extracts. The Pimenta extract of the present invention is typically produced by the known technique of hydrodistillation (steam distillation) of fresh leaves and twigs of plants of *Pimenta racemosa* and berries of *Pimenta dioica*.

Bay or allspice in their commercially available forms are presently preferred, but other forms of Pimenta extract may also be used, e.g., Pimenta extract in a liquid (solvent or another oil), Pimenta extract in an aqueous mixture, Pimenta extract in an aqueous emulsion, Pimenta extract adsorbed onto or absorbed into a solid carrier or substrate, or Pimenta extract associated with other vehicles, provided that such vehicles are compatible with the administration of the Pimenta extract into water harboring the aquatic animal to be treated, and do not adversely affect the aquatic animal being treated or other beneficial aquatic life present in the water.

The Pimenta extract may be introduced directly into water containing the aquatic animal to be treated, but it should be noted that oil extracts, such as West Indian bay oil, are relatively insoluble in water. Nevertheless, the volatile oils can be introduced neat, with subsequent dispersing or after shaking as part of an aqueous mixture. Direct addition of oil extracts to water preferably uses an effective means of dispersion, e.g., high speed or high shear mixing, and such intensive dispersion is preferably carried out in a localized region in the absence of the aquatic animal being treated to avoid injury. A metering or mixing pump, or an inline mixer, e.g., a mixing valve, nozzle or orifice, may be used to accomplish the direct dispersion of oil extracts of Pimenta in water.

A preferred technique for administering the Pimenta extract in this invention involves the use of an aqueous mixture, aqueous emulsion or aqueous dispersion of Pimenta extract that is introduced into the water that will harbor or already is harboring the aquatic animal to be treated. The aqueous mixture, emulsion or dispersion of Pimenta extract is preferably introduced to the water that will contain or already contains the aquatic animal in a manner that ensures further mixing of the mixture, emulsion or dispersion in the water. Such mixing should provide relatively uniform distribution of the Pimenta extract throughout the water, so that the fish or other aquatic animals being treated are continually exposed to the Pimenta extract within the water environment. In a small volume of water, such as a fish hobbyist's fish aquarium, circulation of the water, e.g., via a filter pump or aeration of the water, typically provides sufficient mixing and distribution to maintain an adequate dispersion or mixture of the Pimenta extract throughout the aquarium water. If there is no filter pump or aerator, or if circulation of the aquarium water is otherwise inadequate, the mixture or dispersion of the Pimenta extract may be simply poured in, and the aquarium water gently stirred. For larger volumes of water harboring the fish or other aquatic animals to be treated, additional mechanical mixing may be required. Chemical dispersions, such as emulsions, may also be used, as long as the emulsifiers or dispersants do not adversely affect the beneficial aquatic life in the environment of the aquatic animal being treated.

With respect to the aqueous mixture, emulsion or dispersion containing the Pimenta extract used to treat small volumes of water, e.g., aquariums containing less than about 50 gallons (190 liters), vigorous shaking of Pimenta extract, such as bay oil or allspice oil, and water in a sealed container of less than about 1 gallon (about 3.8 liters) is normally sufficient to provide an aqueous mixture suitable for use by the typical fish hobbyist. The aqueous Pimenta extract mixture may then be introduced into the aquarium water by simply pouring the mixture into the aquarium.

A preferred Pimenta extract composition of this invention is an aqueous mixture containing from about 0.1% to about 20% of the active Pimenta extract, more preferably, from about 0.5% to about 10% Pimenta extract and, most preferably, about 1% to about 5% of the active Pimenta extract, all percentages being by volume, based on the final volume of the composition. The composition is further diluted when added to the water environment containing the fish or other aquatic animals to be treated according to this invention.

Where the Pimenta extract-containing composition includes an oily Pimenta extract, such as bay oil or allspice oil, in water, the composition preferably contains an emulsifier in an amount sufficient to emulsify the oil in water, to provide a relatively stable emulsion, sometimes referred to as a dispersion. Suitable emulsifiers (sometimes called surfactants or dispersants) are those, which are nontoxic and noninjurious to the aquatic animal being treated, and may be cationic, anionic, nonionic or amphoteric emulsifiers. Preferred emulsifiers include, for example, food grade emulsifiers, which are widely available. An overview of some types of suitable emulsifiers is set forth in A. J. St. Angelo, "A Brief Introduction to Food Emulsions and Emulsifiers," at pp. 1–8 of G. Charalambous et al., Eds., *Food Emulsifers— Chemistry, Technology, Functional Properties and Applications,* Elsevier Science Publishing Company Inc., New York, N.Y. (1989), the disclosure of which is hereby incorporated herein by reference.

Nonionic emulsifiers are especially preferred, with Crovol® PK-70 nonionic emulsifier (Croda Inc., Parsippany, N.J., U.S.A.) being a highly preferred water-soluble nonionic emulsifier.

The amount of emulsifier used to provide emulsification of oily Pimenta extract in the aqueous composition is generally not critical, as long as the amount used is sufficient to provide a suitable emulsification or dispersion of the oil phase in the aqueous phase. The concentration of emulsifier may range from about 0.01% to about 20%, more preferably, about 0.1% to about 5%, all percentages being by volume based on the final volume of the composition. For emulsifiers or surfactants that are normally non-liquid, the numerical concentration ranges just noted may be used, with percentages being by weight based on the volume of aqueous emulsion.

Other adjuvants, besides emulsifiers, may also be used, such as antifoaming agents or defoaming agents, antioxidants, preservatives, coloring agents and the like. The adjuvants are typically present in the aqueous Pimenta extract composition in minor amounts, i.e., less than about 5% by volume, and preferably, less than 1% by volume. All such adjuvants should be noninjurious and nontoxic to the fish and other aquatic animals being treated, as well as to other beneficial aquatic organisms present in the water along with the aquatic animal being treated, such as various types of invertebrates and plants.

Particularly preferred stable emulsified aqueous Pimenta extract compositions are as follows:

| | |
|---|---|
| West Indian bay oil or allspice oil | 1% by volume |
| emulsifier | 1% by volume |
| deionized water | 98% by volume |

The emulsifier is preferably Crovol® PK-70 nonionic emulsifier (Croda Inc.). The composition may be prepared by vigorously mixing the oily Pimenta extract and emulsifier in the deionized water, to produce an aqueous emulsion that is stabilized against separation of the oily phase from the aqueous phase. Such mixing may be carried out with a mechanical mixer or by manual shaking.

An aqueous mixture, containing the Pimenta oil, e.g., 1% by volume, can be prepared without the emulsifier, but such an aqueous mixture must be vigorously shaken (for about 1 to about 5 minutes) or mechanically agitated prior to use to disperse the oily extract uniformly throughout the aqueous phase.

Pimenta bay extract and allspice extract, have been found to be extremely effective in providing complete recovery of diseased or injured fish, or other aquatic animals, even when used at low concentrations. For this reason, the present invention includes, as a preferred treatment, introducing the Pimenta extract into the water in which the diseased or injured aquatic animals, or those susceptible to disease or injury, are normally harbored or confined, or into which they will be placed.

In the treatment method of this invention, the Pimenta extract is introduced into the water containing the fish or other aquatic animal to be treated in a dosage amount of from about 0.001 ml (1 microliter) to about 1 ml, preferably from about 0.01 ml (10 microliters) to about 0.5 ml (500 microliters), per day per 10 gallons (37.8 liters) of water to contain or containing the aquatic animal(s) being treated. These amounts are based on the volume of the active Pimenta extract ingredient per se, rather than the amount of the composition containing the Pimenta extract, since the composition contains other components. The amount to use of the composition according to the present invention, containing components or ingredients in addition to the Pimenta extract, can be easily calculated based on the concentration in the composition of the active Pimenta extract ingredient. This dosage may be added to the aquarium or other container or body of water containing, or that will contain, the aquatic animal being treated, as a single dosage each day, as is preferred, or may be added in aliquots of the daily dosage more than once throughout the day.

With the preferred aqueous emulsion composition described above, containing 1% by volume bay or allspice, a preferred daily dosage rate is 10 ml of the aqueous emulsion per 10 gallons (37.8 liters) of water containing the aquatic animal(s) being treated.

The daily treatment dosage is continued for as long as is necessary to provide recovery. Typically, duration of the treatment is at least about three days to about two weeks. Disappearance or amelioration of the outward, visible symptoms or signs of the disease or injury affecting the fish or other aquatic animal, which signs may sometimes include animal behavior, normally indicates successful treatment and recovery of the fish or other aquatic animal from the disease or injury. The treatment duration should desirably include continued daily dosages for about 2 to about 5 days following apparent recovery, to prevent disease recurrence or secondary infection of healed wounds.

The recovery of the diseased or injured aquatic animals, especially fish, from their disease or injury with the treatment method and composition of this invention has been observed to be much faster than the recovery, if the fish recover at all, that results without treatment in accordance with the present invention. Many fish diseases, such as "ragged fins," often cannot be treated successfully with commonly used fish medications, including antibiotics and "salt baths."

In the treatment method of this invention, factors, such as water pH, hardness, alkalinity and the like, do not appear to have any significant effect. The water may be fresh water or may be salt water, a factor normally determined by the fish or other aquatic animal species being treated. Water temperature is maintained within the range that is normally used for the animal species being treated.

The Pimenta extract composition and treatment of this invention are effective for a broad range of bacterial and fungal diseases that typically afflict fish and other aquatic animals. Fish diseases that may be treated in accordance with this invention include bacterial fish diseases, such as fin and tail rot, mouth fungus (often caused by the bacterium *Flavobacterium columnaris*); fungal fish diseases (such as those caused by microorganisms of the genera Saprolegnia and Achyle) and the like. Many fish diseases, it should be noted, are caused by different bacterial or fungal pathogens that often exhibit similar symptoms, so identification of a specific bacterial or fungal pathogen is not usually possible from mere visual inspection of the symptoms on the fish.

Since the Pimenta extract treatment of this invention appears to have broad-spectrum effectiveness against many diseases affecting fish and other aquatic animals, precise identification of specific bacterial or fungal pathogens causing the disease is not usually necessary.

The Pimenta extract composition and treatment of this invention also enhance skin and tissue healing and promote such healing in injured fish or other aquatic animals. Common fish injuries include those resulting from netting, handling or confinement in closed or crowded environments, like shipping containers or holding tanks, in particular, injuries, such as wounds, lacerations, bites from other fish or animals, abrasions, scrapes, burns and other similar damage to skin or other tissues.

The Pimenta extract treatment and composition of this invention are remarkably effective in curing such difficult-to-treat fish diseases, like ragged fins.

The Pimenta extract composition and treatment method of this invention may also be used as a prophylactic or hygienic treatment, to prevent disease-susceptible fish or other aquatic animals from becoming afflicted, or for immediately treating injury-susceptible fish or other aquatic animals when they become injured. The treatment protocol and dosage rates to be used for prophylactic treatment are the same as those described above for the therapeutic treatment of diseased or injured fish and other aquatic animals. For example, fish to be transported in shipping containers may be treated beforehand and during shipping according to this invention to prevent or minimize susceptibility to disease, including aggravation of injuries sustained before or during shipping. As with all medicaments, continuous long-term treatment is not generally recommended, since it creates the risk of developing resistant strains of pathogenic microorganisms that may not be able to be successfully controlled with the medicament.

The fish or other aquatic animals which may be treated according to this invention are typically aquatic animals held in a confined body of water, such as a shipping container, holding tank, aquarium, pool or small pond. Although it is feasible to treat fish or other aquatic animals in large confined bodies of water, e.g., lakes or large ponds, or unconfined water, such as streams, the large quantity of Pimenta extract required in such situations may not be economically practical.

It should be apparent that diseased fish or other diseased aquatic animals can be removed temporarily from their natural or usual habitat of relatively large bodies of water, and relocated into a small confined body of water, specifically for treatment by the method of this invention, and thereafter returned to their natural or usual habitat.

It is also feasible to administer a composition containing Pimenta extract, e.g., an aqueous emulsion of West Indian bay oil or allspice oil, or West Indian bay oil or allspice oil neat, to the fish or other aquatic animal via topical application to the affected sites on the aquatic animal. This technique, however, requires that the affected fish or aquatic animal be temporarily removed from water, and does not lend itself to continuous treatment of the affected aquatic animal over a period of several days. Apparatus that may be used for direct administration of medicaments to fish is described by Johnson in U.S. Pat. No. 4,282,828 and by Kunz et al. in U.S. Pat. No. 4,363,290, both of which are hereby incorporated herein by reference.

Treatment of large numbers or concentrations of fish in breeding or aquaculture ponds is intended to be included as an important application for the preferred method of this invention, in which Pimenta extract is introduced into the water in which the fish are confined.

The present invention is applicable to the treatment of fish and other aquatic animals. The term "fish" as used herein has a wide sense covering various aquatic animals and including, without limitation, fish that are freshwater fish species, saltwater ("marine") fish species, tropical fish species and coldwater fish species. The fish may be adults, juveniles, hatchlings, embryos or eggs, or combinations thereof. The invention is also applicable to treating other aquatic animals besides fish, such as amphibians, e.g., frogs and salamanders, reptiles, e.g., turtles, as well as crustaceans, mollusks, whales, dolphins and the like that may be afflicted with fungal or bacterial diseases, including injuries, analogous to those described above for fish.

The following freshwater fish species have been treated with bay and allspice according to this invention:

| COMMON NAME | SCIENTIFIC NAME |
| --- | --- |
| Common goldfish | Carassius auratus |
| Sumatra barb | Barbus tetrazona tetrazona |
| Bala shark | Balantiochellius melanopterus |
| MacCulochi rainbow fish | Melanotaenia macculochi |
| Black tetra | Gymnocorymbus ternetzi |
| Iridescent shark | Pangasius sutchi |
| Neon tetra | Cheirodon innesi |
| Bleeding heart tetra | Hyphessobrycon erythrostigma |
| Discus | Symphysodon aequifasciata |
| Striped anostomus | Anostomus anostomus |
| Butterfly fish | Pantodon buchholzi |
| Cardinal tetra | Paracheirodon axelrodi |
| Black wedge tetra | Hemigrammus pulcher |
| Clown loach | Botia macracantha |
| Leopard corydoras | Corydoras julii |
| Cherry barb | Barbus titteya |
| Platy | Xiphophorus maculatus |
| Rosy barb | Barbus conchonius |
| Platinum Ogon koi | Cyprinus carpio |
| Zebra danio | Brachydanio rerio |
| Red tailed black shark | Labeo bicolor |
| Marbled hatchetfish | Carnegiella strigata |
| Red rasbora | Rasbora heteromorpha |
| Swordtail | Xiphophorus helleri |
| Flag cichlid | Aequidens curviceps |
| Convict cichlid | Cichlasoma nigrofasciatum |
| Angelfish | Pterophyllum scalare |
| Kissing gourami | Helostoma temmincki |

The following saltwater fish species have been treated with bay and with allspice according to this invention:

| COMMON NAME | SCIENTIFIC NAME |
| --- | --- |
| Black triggerfish | Odonus niger |
| Powder blue tang | Acanthurus leucosternon |
| Yellowtail sailfin tang | Zebrasoma xanthurum |
| Common clownfish | Amphiprion ocellaris |
| Hippo tang | Paracanthurus hepatus |
| Yellow tang | Zebrasoma flavescens |
| Picasso trigger | Rhinecanthus aculeatus |
| Bicolor blenny | Ecsenius bicolor |
| Orchid dottyback | Pseudochromis fridmani |
| Firefish | Nemateleotris magnifica |
| Bicolor cherub | Centropyge bicolor |
| Flame angelfish | Centropyge loriculus |
| Spiny puffer | Diodon holocanthus |
| Queen coris | Coris frerei |
| Line wrasse | Anampses lineatus |
| Lionfish | Pterois volitans |
| Maroon clownfish | Premnas biaculeatus |

-continued

| COMMON NAME | SCIENTIFIC NAME |
| --- | --- |
| Blue damselfish | *Abudefduf cyaneus* |
| Black-saddled puffer | *Canthigaster valentini* |
| Yellow-tailed damselfish | *Chromis xanthurus* |
| Humbug | *Dascyllus aruanus* |
| Royal gramma | *Gramma loreto* |

The treatment method and bay or allspice Pimenta extract composition of this invention not only provide beneficial and surprisingly effective results with the diseased fish or other diseased aquatic animal being treated, but are also highly safe and innocuous to other beneficial aquatic organisms, both flora and fauna, that may typically be present in the water with the treated aquatic animal.

The bay and allspice compositions and treatments described for this invention may be used in combination with other medicaments or healing treatments, if desired, but such other medicaments or treatments are not necessary to obtain the highly efficacious, beneficial results provided by Pimenta extract.

The present invention will now be described and explained further, by reference to the following specific, illustrative, non-limiting Examples.

EXAMPLE 1

Ten adult Japanese Platinum Ogon Koi fish (*Cyprinus carpio*) with severe injuries were treated with bay in this Example 1. The shipping injuries to these fish included multiple large wounds on the side of the fish as well as on the tail peduncle.

The bay composition used in this treatment was an aqueous emulsion containing 1% by volume West Indian bay oil (obtained from Berje Co., Bloomfield, N.J. U.S.A. as "Bay Oil W. I.," 1% by volume Crovol® PK-70 nonionic emulsifier (Croda Inc.), and the balance being deionized water. The bay composition was added to the tank containing the fish, once per day, in an amount of 10 ml per 10 gallons (37.8 liters) of water in the tank.

Total duration of the bay treatment was 7 days. The wounds were observed to close within 48 hours of beginning the treatment. Complete healing occurred after 15 days. Treatment was continued for 5 more days (after the fifteenth day) to prevent any secondary infection of the newly healed surfaces.

EXAMPLE 2

Forty juvenile common fancy goldfish (*Carassius auratus*) having a severe case of "ragged fins" were treated with bay in this Example 2. The bay composition and dosage amount were identical to that described for Example 1.

Total duration of the bay treatment was 10 days. Fin regrowth was visibly apparent 3 days after initiation of the treatment, and complete recovery was observed after 10 days.

EXAMPLE 3

Two adult Black triggerfish (*Odonus niger*) having severe cases of bacterial "eye cloud," characterized by whitish film all over the fishes' eyes, were treated with bay in this Example 3. The bay composition and dosage amount were identical to that described for Example 1.

Total duration of the bay treatment was 10 days. The film on the fishes' eyes was observed to have disappeared after 4 days, and complete recovery was evident after 10 days.

EXAMPLE 4

In an independent university study, bay oil was tested for its efficacy in preventing mortality in experimentally infected goldfish. For each bacterial pathogen, ten infected fish were treated with bay oil composition. The bay treatment utilized the composition and dosage amount described for Example 1. Ten fish were infected by intraperitoneal injection with *Edwardsiella ictaluri* (#6071). Ten fish were infected with *Flavobacterium columnare* (#9). To facilitate the infection, fins of fish were swabbed with 0.1% ammonium hydroxide solution before Flavobacterium was topically applied. Cumulative mortality was determined for each pathogen and compared with the untreated control group. Relative percent survival (the percent cumulative mortality of the control minus the percent cumulative mortality of the treated fish divided by the percent cumulative mortality of the control fish) was calculated for each pathogen. The experiments were terminated when there was 80% mortality in the untreated control group or 100% mortality in treated fish. Mean days to death (mdd) were calculated for each treatment group, and Student's paired t-Tests (the probability that the difference between the treated group and the control group is due to chance, hereinafter referred to as "p") were used to determine statistical differences between treatments and controls. Throughout the experiment, the clinical signs of surviving fish were noted.

In this study, it was determined that bay oil protected the goldfish experimentally infected with $2.7 \times 10^8$ cfu of *Edwardsiella ictaluri*. Relative percent survival was determined to be 80%. Mean days to death were significantly increased for fish treated with bay oil: mdd=5, p=0.0009. Bay oil also protected the goldfish experimentally infected with *Flavobacterium columnare*. Relative percent survival was 50%. Mean days to death were significantly increased for fish treated with bay oil: mdd=3, p=0.02.

These findings indicate that bay oil can be beneficial in treating goldfish diseases associated with *Edwardsiella ictaluri* and *Flavobacterium columnare*. The impressive recovery provided in this Example is particularly illustrative of the unexpected and surprising effectiveness of the method and bay composition of this invention.

EXAMPLE 5

Two Fire-bellied Toads (*Bombina orientalis*), which are aquatic toads that can be maintained in aquaterrariums, having a bacterial disease, were treated with bay in this Example 5. The bay composition and dosage amount were identical to that described for Example 1.

Total duration of the bay treatment was 15 days, after which time recovery was complete.

EXAMPLE 6

Three adult Sumatra barbs (*Barbus tetrazona tetrazona*) having a fungal infection were treated with bay in this Example 6. The bay composition and dosage amount were identical to that described for Example 1.

Total duration of the bay treatment was 10 days. Four days after initiation of the treatment, the fungal "tufts" were observed to have disappeared, and complete recovery was evident after 10 days.

EXAMPLE 7

One painted turtle (*Chrysemys picta*), which is an aquatic turtle that can be maintained in an aquaterrarium and spends much time in the water, having a secondary bacterial infection of a large wound on the neck, was treated with bay in this Example 7. The bay composition and dosage amount were identical to that described for Example 1. The bay composition was introduced into the water pool inside the aquaterrarium.

Total duration of the bay treatment was 8 days, and after this period, recovery was complete.

EXAMPLE 8

Twenty neon tetras (*Cheirodon innesi*), having a bacterial infection named "fin and tail rot," were treated with bay (10 fish) and allspice (10 fish) in this Example 8. The bay composition and dosage amount were identical to that described for Example 1.

The allspice composition used in this treatment was an aqueous emulsion containing 1% by volume allspice oil (obtained from Lebermuth Co., Bremen, Ind., U.S.A. as "Oil, Allspice," 1% by volume Crovol® PK-70 nonionic emulsifier (Croda Inc.), and the balance being deionized water. The bay composition was added to a tank containing ten fish, and the allspice composition was added to a different tank containing ten other fish of the same species. Each composition was added once per day, in an amount of 10 ml per 10 gallons (37.8 liters) of water in the respective tanks.

Total duration of both treatments was 5 days. Two days after initiation of the treatment the fins started to grow back, and complete recovery was evident after 5 days, but in case of the bay treatment fin re-growth was more pronounced.

EXAMPLE 9

Six discus (*Symphysodon aequifasciata*), having a bacterial infection that looked like white patches on the fish's body, were treated with bay (3 fish) and allspice (3 fish) in this Example 9. The bay composition and dosage amount were identical to that described for Example 1. The allspice composition and dosage amount were identical to that described for Example 8.

Total duration of both treatments was 10 days. Five days after initiation of the treatment, white patches disappeared, and complete recovery was evident after 10 days, equal in both cases.

EXAMPLE 10

Two firefish (*Nemateleotris magnifica*), having a bacterial infection named "fin and tail rot," were treated with bay (1 fish) and allspice (1 fish) in this Example 10. The bay composition and dosage amount were identical to that described for Example 1. The allspice composition and dosage amount were identical to that described for Example 8.

Total duration of both treatments was 7 days. Four days after initiation of the treatment, the fins started to grow back, and complete recovery was evident after 5 days, equal in both cases.

EXAMPLE 11

Twenty cardinal tetras (*Paracheirodon axelrodi*), having a bacterial infection named "fin and tail rot," were treated with bay (10 fish) and allspice (10 fish) in this Example 11. The bay composition and dosage amount were identical to that described for Example 1. The allspice composition and dosage amount were identical to that described for Example 8. The respective compositions were added to the respective tanks containing the fish, once per day, in an amount of 10 ml per 10 gallons (37.8 liters) of water in the tank.

Total duration of both treatments was 15 days. Five to seven days after initiation of the treatment, the fins started to grow back, and complete recovery was evident after 15 days, equal in both cases.

EXAMPLE 12

Twelve cherry barbs (*Barbus titteya*), having a bacterial infection named "fin and tail rot" as well as white patches on the body, were treated with bay (6 fish) and allspice (6 fish) in this Example 12. The bay composition and dosage amount were identical to that described for Example 1. The allspice composition and dosage amount were identical to that described for Example 8. Total duration of both treatments was 7 days. Two days after initiation of the treatment patches started to disappear. Three days after initiation of the treatment, the fins started to grow back, and complete recovery was evident after 7 days, equal in both cases.

The present invention may be embodied in other specific forms without departing from the spirit or essential attributes thereof and, accordingly, reference is made to the appended claims, rather than the foregoing specification, as indicating the scope of the invention.

What is claimed is:

1. A therapeutic method for treating a diseased or injured aquatic animal comprising administering to the aquatic animal an oil extract of *Pimenta racemosa* in an amount effective to promote recovery of the diseased or injured aquatic animal.

2. The method according to claim 1 wherein the *Pimenta racemosa* extract is added to water containing or to contain the aquatic animal.

3. The method according to claim 2 wherein the *Pimenta racemosa* extract is added to the water in an amount of about 0.001 ml to about 1 ml of *Pimenta racemosa* extract per day per 10 gallons of water.

4. The method according to claim 2 wherein the *Pimenta racemosa* extract is added to the water in an amount of about 0.01 ml to about 0.5 ml of *Pimenta racemosa* extract per day per 10 gallons of water.

5. The method according to claim 2 wherein the *Pimenta racemosa* extract is added to the water in the form of an aqueous mixture of *Pimenta racemosa* extract in water.

6. The method according to claim 5 wherein the aqueous mixture comprises about 0.5% to about 10% by volume *Pimenta racemosa* extract in water, based on the total volume of the mixture.

7. The method according to claim 5 wherein the aqueous mixture comprises about 1.0% to about 5% by volume *Pimenta racemosa* extract in water, based on the total volume of the mixture.

8. The method according to claim 5 wherein the aqueous mixture comprises from about 0.1% to about 20% by volume *Pimenta racemosa* extract in water, based on the total volume of the mixture.

9. The method according to claim 8 wherein the aqueous mixture further comprises an emulsifier, in an amount sufficient to form an aqueous emulsion of *Pimenta racemosa* extract in water.

10. The method according to claim 9 wherein the emulsifier is a nonionic emulsifier.

11. The method according to claim 9 wherein the aqueous emulsion comprises about 0.1% to about 20% by volume of emulsifier, based on the total volume of the aqueous emulsion.

12. The method according to claim 9 wherein the aqueous emulsion comprises about 0.5% to about 5% by volume

*Pimenta racemosa* extract and about 0.1% to about 5% by volume emulsifier in water, based on the total volume of the aqueous emulsion.

13. The method according to claim 1 wherein the aquatic animal is afflicted with a disease selected from the group consisting of a bacterial disease and fungal disease.

14. The method according to claim 1 wherein the aquatic animal is afflicted with an injury selected from the group consisting of wounds, lacerations, abrasions and burns.

15. The method according to claim 1 wherein the aquatic animal is a fish.

16. A prophylactic method for treating a disease-free aquatic animal comprising adding to water containing or to contain the aquatic animal an oil extract of *Pimenta racemosa* in an amount effective to promote resistance of the aquatic animal to disease.

17. The prophylactic method according to claim 16 wherein the extract is added to the water on the basis of about 0.001 ml to about 1 ml of *Pimenta racemosa* extract per day per 10 gallons of water.

18. The prophylactic method according to claim 16 wherein the aquatic animal is a fish.

19. The prophylactic method according to claim 16 wherein the extract is added to the water in an amount of about 0.01 ml to about 0.5 ml of *Pimenta racemosa* extract per day per 10 gallons of water.

20. The prophylactic method according to claim 16 wherein the *Pimenta racemosa* extract is added to the water in the form of an aqueous mixture of *Pimenta racemosa* extract in water.

21. The prophylactic method according to claim 20 wherein the aqueous mixture comprises about 0.1% to about 20% by volume *Pimenta racemosa* extract in water, based on the total volume of the mixture.

22. The prophylactic method according to claim 20 wherein the aqueous mixture comprises about 0.5% to about 10% by volume *Pimenta racemosa* extract oil in water, based on the total volume of the mixture.

23. The prophylactic method according to claim 20 wherein the aqueous mixture comprises about 1.0% to about 5% by volume *Pimenta racemosa* extract in water, based on the total volume of the mixture.

24. The prophlyactic method according to claim 20 wherein the aqueous mixture further comprises an emulsifier, in an amount sufficient to form an aqueous emulsion of *Pimenta racemosa* extract in water.

25. The method according to claim 24 wherein the emulsifier is a nonionic emulsifier.

26. The prophylactic method according to claim 24 wherein the aqueous emulsion comprises about 0.1% to about 20% by volume of emulsifier, based on the total volume of the aqueous emulsion.

27. The prophylactic method according to claim 24 wherein the aqueous emulsion comprises about 0.5% to about 5% by volume *Pimenta racemosa* extract oil and about 0.1% to about 5% by volume emulsifier in water, based on the total volume of the mixture.

* * * * *